(12) United States Patent
Peck

(10) Patent No.: US 10,238,596 B1
(45) Date of Patent: Mar. 26, 2019

(54) RESTORATIVE FORMULATIONS

(71) Applicant: Dr. Peck's Hair Care Rx LLC, Cypress, TX (US)

(72) Inventor: Stacie Peck, Cypress, TX (US)

(73) Assignee: DR. Peck's Hair Care Rx LLC, Cypress, TX (US)

( * ) Notice: Subject to any disclaimer, the term of this patent is extended or adjusted under 35 U.S.C. 154(b) by 0 days.

(21) Appl. No.: 15/385,700

(22) Filed: Dec. 20, 2016

Related U.S. Application Data

(60) Provisional application No. 62/276,141, filed on Jan. 7, 2016.

(51) Int. Cl.
| | | |
|---|---|---|
| *A61K 36/00* | (2006.01) | |
| *A61K 8/92* | (2006.01) | |
| *A61K 8/97* | (2017.01) | |
| *A61K 8/73* | (2006.01) | |
| *A61K 8/34* | (2006.01) | |
| *A61K 8/67* | (2006.01) | |
| *A61K 8/02* | (2006.01) | |
| *A61Q 7/00* | (2006.01) | |
| *A61K 8/49* | (2006.01) | |

(52) U.S. Cl.
CPC ............ *A61K 8/922* (2013.01); *A61K 8/0216* (2013.01); *A61K 8/345* (2013.01); *A61K 8/4973* (2013.01); *A61K 8/678* (2013.01); *A61K 8/73* (2013.01); *A61K 8/925* (2013.01); *A61K 8/97* (2013.01); *A61Q 7/00* (2013.01)

(58) Field of Classification Search
CPC ..................................................... A61K 36/00
See application file for complete search history.

(56) References Cited

U.S. PATENT DOCUMENTS

| | | | | |
|---|---|---|---|---|
| 2007/0286908 | A1* | 12/2007 | Clampitt | A61K 33/00 424/680 |
| 2010/0196428 | A1* | 8/2010 | Karpov | A61K 8/27 424/401 |
| 2012/0087996 | A1* | 4/2012 | Palmer | A61K 8/97 424/729 |
| 2012/0219518 | A1* | 8/2012 | Serra | A61Q 5/002 424/74 |
| 2013/0209379 | A1* | 8/2013 | Mills | A61K 8/4926 424/59 |
| 2015/0320653 | A1* | 11/2015 | Nguyen | A61K 8/14 424/401 |
| 2016/0058690 | A1* | 3/2016 | Sams | A61K 8/922 424/522 |

* cited by examiner

*Primary Examiner* — Qiuwen Mi
(74) *Attorney, Agent, or Firm* — Patent Law Works LLP

(57) ABSTRACT

The present invention provides regenerative formulations, such as regenerative creams and regenerative oils, methods for the manufacture of the regenerative formulations, and methods for using the regenerative formulations. The regenerative formulations comprise essential oils, moisturizers, stabilizers, preservatives, lubricants, and solvents, and can be used to restore hair.

2 Claims, No Drawings

RESTORATIVE FORMULATIONS

CROSS REFERENCE TO RELATED APPLICATIONS

This application claims priority under 35 USC § 119(e) to U.S. Application No. 62/276,141, entitled "Restorative Formulations" filed on Jan. 7, 2016, the entirety of which is herein incorporated by reference.

FIELD OF INVENTION

The present invention relates to compositions, methods of manufacture and methods of using restorative creams and oils, in particular for restoring hair, promoting hair growth or preventing hair loss.

BACKGROUND

Hair loss can be induced by various causes, for example, reduced metabolic activity of hair roots, reduced physiological activity of the scalp, local disorders of blood circulation which result from a decrease in the amount of blood flowing through the peripheral blood vessels of the subcutaneous tissues of the head, nutritional deficiencies, stress, side effects of drugs, and hereditary factors. For example, the probability of hair loss is greater in people with the gene associated with hair loss. However, age, stress, environmental factors and the like are more closely involved in hair loss. Although hair loss is induced by the above-mentioned causes, little known about the exact causes of hair loss.

Currently commercially available hair growth stimulants and hair growers include vasodilators, e.g., capronium chloride, minoxidil (Rogaine®) and various extracts, hormonal drugs, e.g., estrogen and estradiol, for suppressing the activity of male hormones, and male hormone inhibitors, e.g., pentadecanoic acid and finasteride. The hormonal drugs for suppressing the activity of male hormones and the male hormone inhibitors are clinically ineffective and cause adverse effects, such as erectile dysfunction. Various kinds of drugs, such as Propecia®, tricomin, spironolactone, cyproterone acetate, Nizoral®, cimetidine and oral contraceptive pills, have been introduced into the market, but their effects have proved to be unsatisfactory.

In recent years, drugs for treating and preventing alopecia have been developed and marketed. For example, FDA-approved Rogaine® (minoxidil) and Proscar® (finasteride) for oral administration, which is a drug inhibiting the activity of 5-α-reductase and the subsequent production of dihydrotestosterone, are currently sold as hair growth stimulants. However, these hair growth stimulants are very expensive and are ineffective when applied directly to the scalp. The drugs are limited in their use because of unexpected side effects upon oral administration. Further, hair growth stimulant compositions containing various extracts have been used, such as extracts from many plants including labiatae and asteracease. However, these compositions suffer from the problem of skin trouble upon application on the skin.

Thus, there is a need for regenerative compositions, such as those that stimulate hair growth or prevent hair loss and offer convenience in use without severe adverse effects, such as skin irritation, and erectile dysfunction.

SUMMARY

The present invention provides compositions, method for manufacture, and methods of use of regenerative creams.

The disclosed compositions and methods for hair restoration and hair growth stimulant use natural substances that are non-toxic to patients, such as humans, and do not use hormones or other active compounds that have severe side effects.

In one aspect, disclosed are compositions with regenerative properties the compositions comprising essential oils, moisturizers, stabilizers, preservatives, lubricants, and solvents.

In another aspect, provided are methods for manufacturing restorative formulations, the methods comprising boiling water, placing moisturizers and preservatives in water until melted, cooling to room temperature, adding essential oils, stabilizers, preservatives, lubricants, and solvents, cooling to less than −10° F., and mixing until the restorative cream is obtained. The restorative formulations can be restorative creams or restorative oils.

In another aspect, provided are methods for manufacturing a restorative cream, the method comprising boiling water, placing shea butter, coconut oil, lanolin, vitamin E, avocado oil, and olive and in the water until melted, cooling to room temperature for about 10 minutes, adding water, vegetable glycerin, aloe vera extract, xanthan gum, ylang ylang, optiphen, lavender oil, honey almond fragrance, peppermint oil, rosemary oil, rose water, tea tree, and *eucalyptus* with mixing at low speed until a gelatin forms, cooling the gelatin to less than −10° F. for about 30 minutes, and mixing at high speed for about 30 minutes to provide the restorative cream.

In another aspect, provided are methods for manufacturing a restorative oil, the method comprising mixing shea oil, coconut oil, vitamin E, avocado oil, ylang ylang, optiphen plus, lavender oil, honey almond fragrance, peppermint oil, rosemary oil, rose water, tea tree, and *eucalyptus* with mixing at low speed to provide the restorative oil.

In another aspect, provided are methods of regenerating hair, promoting hair growth or preventing hair loss, the methods comprising applying regenerative cream to the area in need of hair regeneration.

These and other aspects of the present invention will become evident upon reference to the following detailed description.

DETAILED DESCRIPTION

I. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

As used herein, the term "mammal subject" encompasses any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The term "optional" or "optionally" means that the subsequently described event or circumstance may or may not occur, and that the description includes instances where the event or circumstance occurs and instances where it does not.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

As used herein, the terms "treat" or "treatment" are used interchangeably and are meant to ameliorating the disease or disorder (i.e., arresting or reducing the development of the disease or at least one of the clinical symptoms thereof). In one embodiment "treating" or "treatment" refers to ameliorating at least one symptoms of the disease. In another embodiment, "treating" or "treatment" refers to inhibiting the disease or disorder, either physically (e.g., stabilization of a discernible symptom), physiologically, (e.g., stabilization of a physical parameter), or both.

All publications, patents and patent applications cited herein, whether supra or infra, are hereby incorporated by reference in their entirety.

II. Compositions

Disclosed are compositions, method for manufacture, and methods of use of regenerative formulations, such as restorative creams and oils. The disclosed compositions and methods for hair growth stimulant use natural substances that are generally regarded as safe for humans (GRAS), that are non-toxic to mammal subjects, such as humans, and do not use hormones or other active compounds that have severe side effects.

In one aspect, disclosed are compositions with regenerative properties the compositions comprising essential oils, moisturizers, stabilizers, preservatives, lubricants, and solvents.

The essential oils can be any of the essential oils known to one of skill in the art. Generally, essential oils are volatile aromatic oils derived from plants through distillation, but can be prepared synthetically. Essential oils are known to be environmentally friendly. Essential oils for use in the present invention can by purchased from a commercial source, synthesized, or derived from herbs, flowers, trees, and other plants by methods known to those of skill in the art (e.g., steam distillation, enfleurage (i.e., extraction using fat(s)), maceration, solvent extraction, or mechanical pressing). For example, Shea Butter is a natural butter or naturally occurring fat extracted from the nuts of the Shea fruits using a suitable extraction solvent. Shea oil is similarly obtained. Shea butter is exceptionally rich and contains fatty acids that stimulate the skin's natural renewal processes and replenish lost oils to the scalp and hair, leaving it healthy and shiny. Shea butter and oil imparts beneficial properties as a moisturizer and emollient to protect skin from dehydration and other climatic influences, improves appearance of dry, irritated skin by restoring suppleness and smoothness and may act as an anti-inflammatory agent. Shea butter is absorbed quickly and completely into the scalp without clogging pores, without leaving a greasy residue, and without causing build-up of oil or dandruff. Shea butter is a solid at room temperature and can be used in the preparation of restorative creams, while Shea oil is a liquid at room temperature and can be used in the preparation of restorative oils. As another example, argan contains essential fatty acids, which are known for its moisturizing and antioxidant properties. Argan oil can help a user avoid split ends and restore damaged hair. Other benefits of argan oil health include adding luster to dull hair, improving elasticity, and reducing hair loss due to breakage.

Examples of suitable essential oils for use in the present invention may include, for instance, anise oil argan oil, *artemisia* oil, lemon oil, orange oil, oregano oil, rosemary oil, wintergreen oil, thyme oil, lavender oil, clove oil, hops oil, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, *eucalyptus* oil, vervain oil, peppermint oil, gum benzoin oil, basil oil, fennel oil, fir oil, balsam oil, mint oil, ocmeaoriganum oil, Hydastiscarradensis oil, Berberidaceaedaceae oil, Ratanhiae and *Curcuma longa* oil, sesame oil, macadamia nut oil, evening primrose oil, Spanish sage oil, Spanish rosemary oil, coriander oil, pimento berries oil, rose oil, bergamot oil, rosewood oil, chamomile oil, sage oil, clary sage oil, cypress oil, sea fennel oil, frankincense oil, ginger oil, grapefruit oil, grape seed oil, jasmine oil, juniper oil, lime oil, mandarin oil, marjoram oil, myrrh oil, neroli oil, patchouli oil, pepper oil, black pepper oil, petitgrain oil, pine oil, grape seed oil, rose otto oil, Shea oil, Shea butter, spearmint oil, spikenard oil, vetiver oil, or ylang ylang oil. In particular, essential oils such as Shea oil or Shea butter, ylang ylang, lavender oil, honey almond fragrance, peppermint oil, rosemary oil, tea tree oil, *eucalyptus* oil, and combinations thereof can be used in the practice of the invention. Still other essential oils known to those of skill in the art are also contemplated as being useful within the context of the present invention.

Suitable moisturizers for use in the present invention include, but are not limited to, aloe vera, glycerin, water soluble polyols, propylene glycol, polyethylene glycol, polypropylene glycol, sorbitol, and pantothenol, and the like or a combination of two or more thereof. Suitable polyols include glycerin, sorbitol, mannitol, maltitol, isomalt, xylitol, and erythritol. In some embodiments the moisturizer is aloe vera. Other moisturizers include mineral oil. In some embodiments, the aloe vera is aloe barbadensis leaf extract (e.g., pure aloe barbadensis leaf extract). The aloe vera can be in the form of a gel or liquid or any other suitable form. In some embodiments, the aloe vera is present as aloe vera liquid. In addition to moisturizing, the polysaccharides such as glucomannan and acemannan present in aloe vera may impart other beneficial properties to the composition such as antibiotic, anti-inflammatory, wound healing, soothing and calming of skin. In particular, moisturizers such as Shea butter, Shea oil, vegetable glycerin, coconut oil, aloe vera extract, avocado oil, olive oil, and combinations thereof can be used in the practice of the invention.

The compositions of the invention can contain stabilizers, such as those described in Remington's Pharmaceutical Sciences 16th edition, Osol, A. Ed. (1980). Thus, the stabilizers can be Polysorbate 60, Polysorbate 20, Xanthan gum, and combinations thereof.

In some embodiments, the preservatives utilized in the present compositions include any suitable preservatives known in the art, including cosmetic grade preservatives. The preservatives may also function as antioxidants. Suitable preservatives include, but are not limited to, optiphen, Vitamin E, parabens, phenoxyethanol, caprylyl glycol, sorbic acid, glucono lactone, sodium benzoate boric acid or its salts such as sodium borate and potassium borate, sodium acid pyrophosphate, potassium pyrophosphate, sodium benzoate, calcium benzoate, potassium benzoate, potassium sorbate, sodium sorbate, calcium sorbate, sodium acetate, calcium acetate, sodium diacetate, calcium diacetate, sodium propionate, calcium propionate, potassium propionate, niacin, citric acid, sorbic acid, sodium propinate, paraaminobenzoic acid esters (parabens) and the like or mixtures thereof. Vitamin E can act as an anti-oxidizing agent that helps to stabilize oils and prevent rancidity.

Vitamin E also has anti-oxidizing properties for the skin, promotes healing, and improves circulation within the scalp. Any typical preservative or mixtures thereof used in the personal care or cosmetic industry can be used in the practice of the invention.

The compositions of the invention can include aqueous or nonaqueous solutions. Examples of nonaqueous solvents are polypropylene glycol, polyethylene glycol, vegetable oils such as olive oil, sesame oil, coconut oil, *arachis* oil, peanut oil, mineral oil, avocado oil, tree oil, rosemary oil, organic esters such as ethyl oleate, or fixed oils including synthetic mono or di-glycerides. Aqueous solvents include water, alcoholic/aqueous solutions, emulsions or suspensions, including saline and buffered media. In particular, the solvents can be water, Rose water, avocado oil, rosemary oil, tree oil, olive oil, and combinations thereof.

The compositions of the invention can include a lubricant or an emollient. Suitable lubricants include, but are not limited to lanolin, glycerol, lanolin derivatives mineral oil, petrolatum, cholesterol, isostearyl neopentanoate, octyl stearate, mineral oil, isocetyl stearate, myristyl myristate, octyl dodecanol, dimethicone, phenyl trimethicone, cyclomethicone, dimethiconol, propylene glycol, lactic acid, butylene glycol, sodium PCA, carbowax, castor oil, squalane, silicons such as dimethicone, cyclomethicone, simethicone, and urea or a combination of two or more thereof. Suitable lanolin derivatives include, for example, lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin, In some embodiments, the lubricant is selected from the group consisting of lanolin, lanolin derivatives mineral oil, petrolatum, castor oil, squalane, and silicons or a combination of two or more thereof. Lanolin is a wax secreted by the sebaceous glands of wool-bearing animals. Lanolin is a lubricant with moisturizing properties. It may also act as an emulsifier since it has high water absorption capability. Lanolin may soothe and protect dry cracked skin, provide effective moisture barrier, and offer immediate relief from discomfort. Thus, in some aspects, the composition can contain lanolin.

Optionally, the pH of the composition may also be controlled within a range that is considered more biocompatible. For instance, it is typically desired that the pH is within a range of from about 3 to about 9, in some embodiments from about 4 to about 8, and in some embodiments, from about 5 to about 7. Various pH modifiers may optionally be utilized in the composition to achieve the desired pH level. Some examples of pH modifiers that may be used in the present invention include, but are not limited to, mineral acids, sulfonic acids (e.g., 2-[N-morpholino]ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. When utilized, the pH modifier may be present in any effective amount needed to achieve the desired pH level.

To better enhance the benefits to consumers, other optional ingredients may also be used. For instance, some classes of ingredients that may be used include, but are not limited to: antioxidants (product integrity); anti-reddening agents; astringents-cosmetic (induce a tightening or tingling sensation on skin); colorants (impart color to the product); deodorants (reduce or eliminate unpleasant odor and protect against the formation of malodor on body surfaces, by, for example, absorption, adsorption, or masking); fragrances (consumer appeal); opacifiers (reduce the clarity or transparent appearance of the product); skin conditioning agents; skin exfoliating agents (ingredients that increase the rate of skin cell turnover such as α-hydroxyacids and β-hydroxyacids); skin protectants (a drug product which protects injured or exposed skin from harmful or annoying stimuli); and viscosity modifiers (e.g., thickeners to increase viscosity).

III. Manufacture

The restorative compositions described above can be manufactured by methods described herein. For example, the restorative cream can be manufactured by placing moisturizers and preservatives in a container capable of conducting heat, heating the container until the contents are melted, cooling to room temperature, adding essential oils, stabilizers, preservatives, and lubricants, cooling to less than about 32° F., preferably less than about −10° F., more preferably less than about −20° F., and mixing until the restorative cream is obtained. The contents can be heated to the desired temperature using any of the known contact or non-contact methods, such as for example, using a heater including, but not limited to, a microwave heater, an infrared heater, an induction heater, a micathermic heater, a solar heater, a heat exchanger, a gas heater, a plasma heater, a lamp heater, an infrared heater or any combination thereof. The restorative oil can be manufactured by placing moisturizers and preservatives in a container and mixing to obtain a uniform liquid, adding essential oils, stabilizers, preservatives, and lubricants, and mixing until the restorative oil is obtained.

The essential oils component of the present composition can be present in an amount from about 2% to about 35% of the total volume of the composition, preferably about from about 3% to about 10% of the total volume, more preferably from about 4% to about 8% of the total volume.

The moisturizers component of the present composition can be present in an amount from about 10% to about 90% of the total volume of the composition, preferably about from about 30% to about 80% of the total volume, more preferably from about 40% to about 70% of the total volume.

The stabilizers component of the present composition can be present in an amount from about 0.5% to about 15% of the total volume of the composition, preferably about from about 1% to about 4% of the total volume, more preferably from about 1% to about 3% of the total volume.

The preservatives component of the present composition can be present in an amount from about 0.5% to about 25% of the total volume of the composition, preferably about from about 1% to about 10% of the total volume, more preferably from about 2% to about 8% of the total volume.

The lubricants component of the present composition can be present in an amount from about 1% to about 25% of the total volume of the composition, preferably about from about 2% to about 10% of the total volume, more preferably from about 3% to about 8% of the total volume.

The restorative composition, once manufactured, can be packaged for sale. Thus, the method further includes packaging the topical composition using suitable packaging methods known in the art using suitable packaging materials. As used herein, the term packaging material means any component of packaging in which the topical composition is contained. Packaging materials include, for example, polymer containers, tubes or glass containers, labels placed on or in packaging or on product, adhesives used to close or seal packaging or adhere labels and the like thereto; ink printed directly on product, directly on packaging, or on a label that is then adhered to packaging. In some embodiments, the packaging includes aseptic packaging. In some embodiments, the product is individually packed, (e.g., in individual cosmetic jars, in individual tubes, plastic bags, bottles, sealed foils, etc.) and then collectively packed in bulk boxes. The packaged product can be stored.

VI. Use

In certain aspects of the invention, a composition such as those described herein can be administered to a subject, such as a mammalian subject or a human subject, by rubbing it on the skin of the subject, e.g., in areas located at or at least within the vicinity of a desired target area. For example, the composition can be applied by rubbing the composition topically against the skin, which allows the composition to be absorbed by the skin. The composition can be applied once, or more than once. For example, the composition may be administered at predetermined intervals. In some embodiments, for instance, the composition may be applied once per day, twice per day, 3 times per day, 4 times per day, once every other day, once every three days, once every four days, etc. The amount of the composition necessary to bring about the therapeutic treatment is not fixed, and may depend upon factors such as the desired outcome, the type and severity the disease or condition, and the like. Thus, the restorative cream or the restorative oil of the invention can be applied sparingly to dry or damp hair, without rinsing, once or twice daily.

In certain embodiments of the invention, the administration of various compositions of the invention may be designed so as to result in sequential exposures to the composition over a certain time period, for example, hours, days, weeks, months, or years. This may be accomplished, for example, by repeated administrations of a composition of the invention by one or more of the methods described herein.

EXAMPLES

The examples below are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Manufacture of the Restorative Cream:

The components of the restorative cream are given in Table 1 below:

TABLE 1 the composition of restorative cream.

| Component | Volume (mL) |
|---|---|
| Water | 600 |
| Shea Butter | 480 |
| Vegetable Glycerin | 400 |
| Coconut oil | 300 |
| Aloe Vera Extract | 200 |
| Lanolin | 100 |
| Vitamin E | 100 |
| Xantham Gum | 45 |
| Honey Almond Fragrance | 30 |
| Optiphen Plus | 30 |
| Polysorbate 20 | 30 |
| Ylang Ylang | 24 |
| Avocado Oil | 20 |
| Olive oil | 20 |
| Guar gum | 15 |
| Lavender oil | 12 |
| Peppermint oil | 10 |
| Rosemary oil | 10 |
| Rose water | 8 |
| Tea Tree oil | 6 |
| Eucalyptus oil | 2 |

Shea butter, coconut oil, lanolin, vitamin E, avocado oil, and olive oil were placed in a container that can conduct heat. The container was heated to melt the contents by placing it on top of the boiling water. The container was then removed from the heat source, and allowed to cool to room temperature for about 5 to 10 minutes. The remaining ingredients were then added to the container, and the contents were mixed at low speed to form a gelatin. The gelatin was cooled at −23° F. for about 20 to 30 minutes to harden the gelatin. The hardened gelatin was then mixed at high speed for about 30 minutes to give about 80 ounces of the restorative cream.

Example 2

Manufacture of the Restorative Oil:

The components of the restorative oil are given in Table 2 below:

TABLE 2 the composition of restorative oil.

| Component | Volume (mL) |
|---|---|
| Olive oil | 180 |
| Coconut oil | 100 |
| Shea oil | 60 |
| Avocado oil | 56 |
| Argan oil | 30 |
| Vitamin E | 20 |
| Optiphen Plus | 8 |
| Polysorbate 20 | 8 |
| Ylang Ylang | 6 |
| Lavender oil | 3 |
| Peppermint oil | 2.5 |
| Rosemary oil | 2.5 |
| Rose water | 2 |
| Tea Tree | 1.5 |
| Eucalyptus | 0.5 |

Shea oil, coconut oil, vitamin E, avocado oil, and olive oil were placed in a container and mixed at room temperature. If needed, the container and its contents can be heated as described above in Example 1, wherein a homogeneous solution results. The remaining ingredients were then added to the container, and the contents were mixed at low speed to form the restorative oil.

Example 3

Use of the Restorative Cream or Oil:

This example illustrates the use of the restorative cream or the restorative oil to restore hair. The restorative cream was prepared according to Example 1, while the restorative oil was prepared according to Example 2. A subject sparingly applies the cream or oil to dry or damp hair once a day for several months. Each person serves as their own control. After a period of time, the subject notices restoration of hair where the cream or oil was applied.

While the invention has been particularly shown and described with reference to a preferred embodiment and various alternate embodiments, it will be understood by persons skilled in the relevant art that various changes in form and details can be made therein without departing from the spirit and scope of the invention.

I claim:

1. A restorative cream comprising:
24.6%/v water;
19.7%/v shea butter;
16.4%/v vegetable glycerin;
12.3%/v coconut oil;
8.2%/v aloe vera extract;
4.1%/v lanolin;
4.1%/v vitamin E;
1.8%/v xanthan gum;
1.2%/v almond fragrance;
1.2%/v a composition comprising sorbic acid, caprylyl glycol, and phenoxyethanol;
1.2%/v polysorbate 20;
1%/v ylang ylang;
0.8%/v avocado oil;
0.8%/v olive oil;
0.6%/v guar gum;
0.5%/v lavender oil;
0.4%/v peppermint oil;
0.4%/v rosemary oil;
0.3%/v rose water;
0.2%/v tee tree oil; and
0.1%/v *eucalyptus* oil.

2. A restorative oil comprising:
37.5%/v olive oil;
20.8%/v coconut oil;
12.5%/v shea oil;
11.7%/v avocado oil;
6.3%/v argan oil;
4.2%/v vitamin E;
1.7%/v a composition comprising sorbic acid, caprylyl glycol, and phenoxyethanol;
1.7%/v polysorbate 20;
1.2%/v ylang ylang;
0.6%/v lavender oil;
0.5%/v peppermint oil;
0.5%/v rosemary oil;
0.4%/v rose water;
0.3%/v tee tree oil; and
0.1%/v *eucalyptus* oil;
wherein the vitamin E, sorbic acid, caprylyl glycol, and phenoxyethanol act as a preservatives.

* * * * *